United States Patent
Caspari et al.

(10) Patent No.: US 6,290,711 B1
(45) Date of Patent: Sep. 18, 2001

(54) CONNECTOR DEVICE AND METHOD FOR SURGICALLY JOINING AND SECURING FLEXIBLE TISSUE REPAIR MEMBERS

(75) Inventors: Richard B. Caspari, Maidens, VA (US); Daniel F. Justin, Logan, UT (US)

(73) Assignee: Innovasive Devices, Inc., Logan, UT (US)

( * ) Notice: Subject to any disclaimer, the term of this patent is extended or adjusted under 35 U.S.C. 154(b) by 0 days.

(21) Appl. No.: 09/374,727

(22) Filed: Aug. 13, 1999

(51) Int. Cl.[7] .................................................. A61B 17/04
(52) U.S. Cl. ............................................. 606/232; 606/72
(58) Field of Search ........................................ 606/232, 72

(56) References Cited

U.S. PATENT DOCUMENTS

| | | | |
|---|---|---|---|
| 3,910,281 | * 10/1975 | Kletachka | 606/232 |
| 4,505,274 | * 3/1985 | Speelman | 606/221 |
| 5,062,846 | * 11/1991 | Oh et al. | 606/158 |
| 5,078,731 | * 1/1992 | Hayhurst | 606/232 |
| 5,100,417 | 3/1992 | Cerier et al. | 606/139 |
| 5,160,339 | * 11/1992 | Chen et al. | 606/158 |
| 5,171,251 | * 12/1992 | Bregen et al. | 606/151 |
| 5,222,976 | 6/1993 | Yoon | 606/223 |
| 5,234,449 | * 8/1993 | Bruker et al. | 606/158 |
| 5,268,001 | 12/1993 | Nicholson et al. | 606/72 |
| 5,282,832 | * 2/1994 | Toso et al. | 606/232 |
| 5,330,442 | * 7/1994 | Green et al. | 606/232 |
| 5,376,101 | * 12/1994 | Green et al. | 606/232 |
| 5,383,905 | 1/1995 | Golds et al. | 606/232 |
| 5,409,499 | * 4/1995 | Yi | 606/151 |
| 5,413,585 | * 5/1995 | Pagedas | 606/232 |
| 5,423,860 | 6/1995 | Lizardi et al. | 606/232 |
| 5,474,572 | * 12/1995 | Hayhurst | 606/232 |
| 5,514,159 | 5/1996 | Matula et al. . | |
| 5,520,702 | 5/1996 | Sauer et al. | 606/232 |
| 5,531,763 | * 7/1996 | Mastri et al. | 606/148 |
| 5,630,824 | 5/1997 | Hart | 606/232 |
| 5,649,963 | 7/1997 | McDevitt | 606/232 |
| 5,681,351 | 10/1997 | Jamiolkowski et al. . | |
| 5,702,398 | * 12/1997 | Tarabishy | 606/72 |
| 5,899,921 | * 5/1999 | Caspri et al. | 606/232 |
| 5,902,321 | * 5/1999 | Caspri et al. | 606/232 |
| 5,957,953 | * 9/1999 | DiPoto et al. | 606/232 |
| 5,968,078 | * 10/1999 | Grotz | 606/232 |
| 6,056,751 | * 5/2000 | Fenton | 606/72 |

FOREIGN PATENT DOCUMENTS

| | | |
|---|---|---|
| 29613728U1 | 8/1996 | (DE) . |
| 0634142 A2 | 1/1995 | (EP) . |
| 2682867 | 4/1993 | (FR) . |

* cited by examiner

*Primary Examiner*—Gary Jackson
(74) *Attorney, Agent, or Firm*—Allen, Dyer, Doppelt, Milbrath & Gilchrist, P.A.

(57) ABSTRACT

A connector for joining sections of flexible material includes a locking member that has an engagement portion at a distal end and that can support a flexible member at a proximal end. An outer member is engageable with the locking member's engagement portion and is movable between a disengaged position and a locking position in cooperation with the locking member. When the outer member is in the locking position, the flexible material piece is retainable along the nonlinear path against movement between the locking member and the outer member. The connector is lockable at a desired surgical site in a generally collinear fashion with the flexible material piece. The nonlinear pathway defined by the material enhances the strength of the connection, which is particularly effective in the case of suture material, which is known to slip easily. The piece of material to be secured may include one or more pieces of suture or a loop of suture having two ends, or sections of wire, cable, or tissue pieces.

17 Claims, 4 Drawing Sheets

CONNECTOR DEVICE AND METHOD FOR SURGICALLY JOINING AND SECURING FLEXIBLE TISSUE REPAIR MEMBERS

FIELD OF THE INVENTION

This invention relates to a surgical connector and method for the tightening, joining, and securing of flexible members without tying knots.

RELATED ART

With the advent of endoscopic surgical techniques such as arthroscopy, laparoscopy, gastroentroscopy, and laryngoscopy, surgeons are able to access, visualize, and operate on surgical sites from new perspectives. Endoscopic, laparoscopic, and arthroscopic surgery relies on small-diameter cannulas that extend through small incisions made through the skin into a surgical site. In an endoscopic procedure, a video camera having a small-diameter lens is inserted through a trocar tube that is passed through an incision and permits visual inspection and magnification of the surgical site. Small-diameter flexible instruments can then be manipulated to the repair site through additional cannulas. These instruments permit the surgeon to precisely prepare the tissue that is to be repaired or joined together. However, with few exceptions, such as tissue staples or laser fusion tissue is still repaired by stitching with suture.

Currently, an effective and often-used method of surgically tightening and joining suture or other flexible tissue repair members together is by tying knots. Various devices have been developed to assist the surgeon in tying knots during surgical procedures, including suture and surgical clip-type devices that may, however, be too large to use in the confined space available in an endoscopic procedure. Such suture clip and surgical clip devices generally include one-piece bendable arrangements having hinged mechanisms where two ends thereof are brought together to enclose the suture and are locked thereto. Examples of such devices are shown in U.S. Pat. Nos. 5,474,572 to Hayhurst; 5,409,499 to Yo; 5,330,442 to Green et al.; 5,234,449 to Bruker et al.; 5,171,251 to Bregen et al.; 5,160,339 to Chen et al.; 5,078,731 to Hayhurst; and 5,062,846 to Oh. Additional, a number of nonhinged suture locking devices have been developed, such as U.S. Pat. Nos. 5,531,763 to Mastri et al.; 5,413,585 to Pagedas; 5,282,832 to Toso et al.; 5,376,101 to Green et al.; 4,505,274 to Speelman; and 3,910,281 to Kletschka et al. Golds et al. (U.S. Pat. No. 5,383,905) describes a suture loop securing device having relatively slidable members for securing ends of a suture loop in a generally collinear fashion.

In-line tensioning and the joining of a flexible member, with the flexible member describing a nonlinear path through the device, is provided by Caspari et al. (U.S. Pat. Nos. 5,899,921 and 5,902,321).

For use in endoscopy and like procedures, devices such as knot pushers have been designed to assist in tying knots endoscopically. Examples of such devices designed to assist with arthroscopic knot tying include commercially available knot pushers such as disclosed in U.S. Pat. Nos. 5,217,471 to Burkhart and 5,562,684 to Kammerer.

In endoscopic surgery, even with these devices, knot tying is time consuming, difficult, and may produce a knot or knots that lack adequate holding strength or tightness. Accordingly, although conventional knot-tying methods may be adequate for open surgical procedures where the suture can be pulled, as with direct in-line access and visualization, and even where the flexible members or both ends of the same member can be joined with tightly applied knots, it is not necessarily optimal to join flexible members together with knots during endoscopic procedures. Due to the dimensional constraints of endoscopy, knots tied through cannulas tend not to be as tight as knots tied through open surgical techniques. Also, because the surgical sites tend to be smaller in endoscopic procedures than in open procedures, multiple knot throws are often needed to secure the knots. Accordingly, endoscopic knots tend to be significantly proportionately larger than knots tied during open procedures with respect to a small surgical site. This combination of a formation of a relatively large, loose knot in a small hard-to-access surgical site introduces potential surgical difficulties that may affect the procedure outcome. Additionally, such knot-tying procedures can be time consuming and may require advanced endoscopic technical experience to effectively join the tissue together tightly. Also, it is desirable to provide a knot having a verifiable hold. Thus a device that securely, efficiently, and effectively joins together two or more ends of flexible tissue repair members as used in soft tissue repair, such as a suture, is needed during both open and endoscopic procedures.

In addition to the above, the issue of joining suture together endoscopically without the use of knots has been addressed, for example, by Hart (U.S. Pat. No. 5,630,824), Sauer et al. (U.S. Pat. No. 5,520,702), Matula et al. (U.S. Pat. No. 5,514,159), and Golds et al. ('905).

The above examples relate mainly to the joining of sutures endoscopically, although it should be understood that it would be desirable to provide a device that surgically joins together other flexible members such as cable, wire, bands, or other flexible members used to join tissue together. A number of such devices are currently available, with an example disclosed in U.S. Pat. No. 4,050,464 to Hall.

Heretofore, surgeons have lacked the ability to join together two or more dissimilar flexible members where a use of knots for such joining has not been possible due to different mechanical and physical properties of the flexible members, or where space has not been available, or where needed crimps or clips have not been available to join flexible members having different properties. A device that is specifically designed to join together different types of flexible members could therefore potentially open new areas of surgical procedures. With such a device, a surgeon could then repair a soft tissue, such as ligament, with suture and repair a harder tissue, such as bone, with a more rigid band. Accordingly, it is recognized that a device that could then join together the two flexible members of different properties would be an asset to the surgical community.

Additionally, it is further recognized that it would be desirable directly to join together flexible tissue, such as ligaments. Earlier surgical staples and clips have been developed for such purposes, as, for example, the devices shown in U.S. Pat. Nos. 4,505,273 to Braun and 5,222,975 to Crainich. Alternatives to suture for joining tissue are shown in U.S. Pat. Nos. 4,955,913 to Robinson and U.S. Pat. Nos. 5,222,976 to Yoon and 5,123,913 to Wilk et al. Heretofore, as needed, ends of ruptured long flexible tissue, such as ligaments, have been temporarily joined together, typically by a mechanical means, until the tissue heals biologically.

Heretofore, various devices have been developed that have attempted to overcome the disadvantages of conventional suture and knots. Such have included staples, clips, clamps, or other fasteners. Additionally, it has been attempted to join tissue using suture during endoscopic surgery, such as by cinching or crimping suture ends or segments together. No device or method has been known that combines the following three functions: in-line tightening of the flexible member prior to joining; a change in the direction of the flexible member during and after joining; and a capability for additional tightening of the flexible member during joining.

SUMMARY OF THE INVENTION

It is an object of the present invention to provide a device for use in an endoscopic procedure that will allow for an in-line joining and tightening of one or more flexible members.

It is another object to provide such a device that permits the flexible member(s) to be additionally tightened, as needed, as the device is engaged.

Another object of the present invention is to provide a device that is capable of joining sections of tissue to be noncollinear with a tension on a flexible member, providing for a mechanically stable engagement.

A further object of the present invention is to provide a device comprising locking and outer members arranged such that the locking member will allow a flexible member to pass in line through its center, during tightening, with an outer member having an inside surface commensurate with that of the locking member outside surface so as to be moved thereover to lock the flexible member between the locking and outer member opposing or shared surfaces.

An additional object of the present invention is to provide such a device that is releasable from the flexible material without damage thereto if it is desired to reverse or remake the connection.

Yet another object of the present invention is to provide for joining a plurality of flexible members that may be alike or physically different, and where each member is passed within the locking member and are, individually or together, passed back between the opposing or shared surfaces of the locking and outer members.

Still another object of the present invention is to provide an instrument for delivery of the device and a method for its use to join flexible members in an endoscopic surgical procedure.

Still another object of the present invention is to provide a device and an instrument for delivering the device that are easily and conveniently used in an endoscopic surgical procedure for permanently joining flexible members together.

The present invention has particular application to the surgical joining of flexible members, such as suture, that may comprise one piece of material, both ends of the same member, or a plurality of flexible pieces. Securing of flexible pieces of material, such as cable and wire, is possible without twisting or joining the pieces together or using crimps. It is possible to secure more than two strands of the same flexible material or both ends of the same member during a suture stitching procedure, and also directly to join flexible bodily tissues.

Another application is for affixing a single piece of flexible material at a desired site during a surgical procedure, particularly an endoscopic procedure.

A particular advantage of the present invention is that the connector is applied in the direction of the suture route, rather than transverse to it, and a lower-profile connector is provided. This feature is particularly useful in endoscopy, where space is limited.

These and other objects are achieved by the connector and driver of the present invention, which obviate the need for tying knots or forming a permanent connection such as a crimp. In a preferred embodiment, the connector comprises a locking member that has an engagement portion at a distal end and means for supporting a flexible member at a proximal end. An outer member has means for receiving the locking member engagement portion. The outer member is movable between a disengaged position and a locking position in cooperation with the flexible member supporting means.

The connector further comprises means for causing a piece of flexible material to achieve a nonlinear path relative to the locking member's engagement portion and the outer member receiving means. When the outer member is in the locking position, the flexible material piece is retainable along the nonlinear path against movement between the locking member and the outer member. The causing means is further adapted to permit a placement and a locking of the outer member and the locking member at a desired surgical site in a generally collinear fashion with the flexible material piece.

The nonlinear pathway defined by the material enhances the strength of the connection, which is particularly effective in the case of suture material, which is known to slip easily. The locking position achieves a connection in line with the material, which permits a longitudinal force to be used in forming the connection. This is particularly advantageous in endoscopic applications, where space is limited. Also, attachments that require securing by a perpendicular approach necessitate an additional tool and incision.

The nonlinear path further creates an additional tightening force during the forming of the connection, since the material pathway is lengthened during the mating between the locking and outer members.

The piece of material to be secured may include one or more pieces of suture or a loop of suture having two ends, although this is not intended as a limitation. The connector is also usable for securing sections of wire or cable or tissue pieces.

Another important feature of the present invention is the reversible nature of the engagement. If the user wishes to release the connection, the locking member is disengagable from the outer member.

The locking member is adapted to allow the flexible material to pass in line during tightening. So arranged, the locking member is free to move along the flexible member and therefore can be moved into direct contact with a section of tissue, bone, or the like.

The invention also includes a delivery instrument and method for its use to allow for the delivery of the device to a body site and to be operated to join flexible members surgically. The instrument is designed to hold the locking and outer members securely while the flexible member is introduced.

One instrument embodiment provides an extension to the locking member in the form, for example, of an elongated shaft portion frangibly attached to the locking member, which can be manipulated for insertion and broken off following locking of the flexible material. The shaft portion in one embodiment has means for attaching to an instrument at a distal end.

DETAILED DESCRIPTION OF THE PREFERRED EMBODIMENT

A description of the preferred embodiments of the present invention will now be presented with reference to FIGS. 1–4.

The connectors to be disclosed herein can be used to join together, permanently or temporarily, two or more sections of flexible materials, such as sutures, wires, cable, tissue pieces, or the like, at a location where it is necessary to place the connected junction into a close-fitting location or against a bone surface. The connectors can also be used to secure one section of flexible material at a desired location. The materials to be connected may be physically unlike and are securely connected together by joining of members of the connecting device of the invention.

Figure 1:
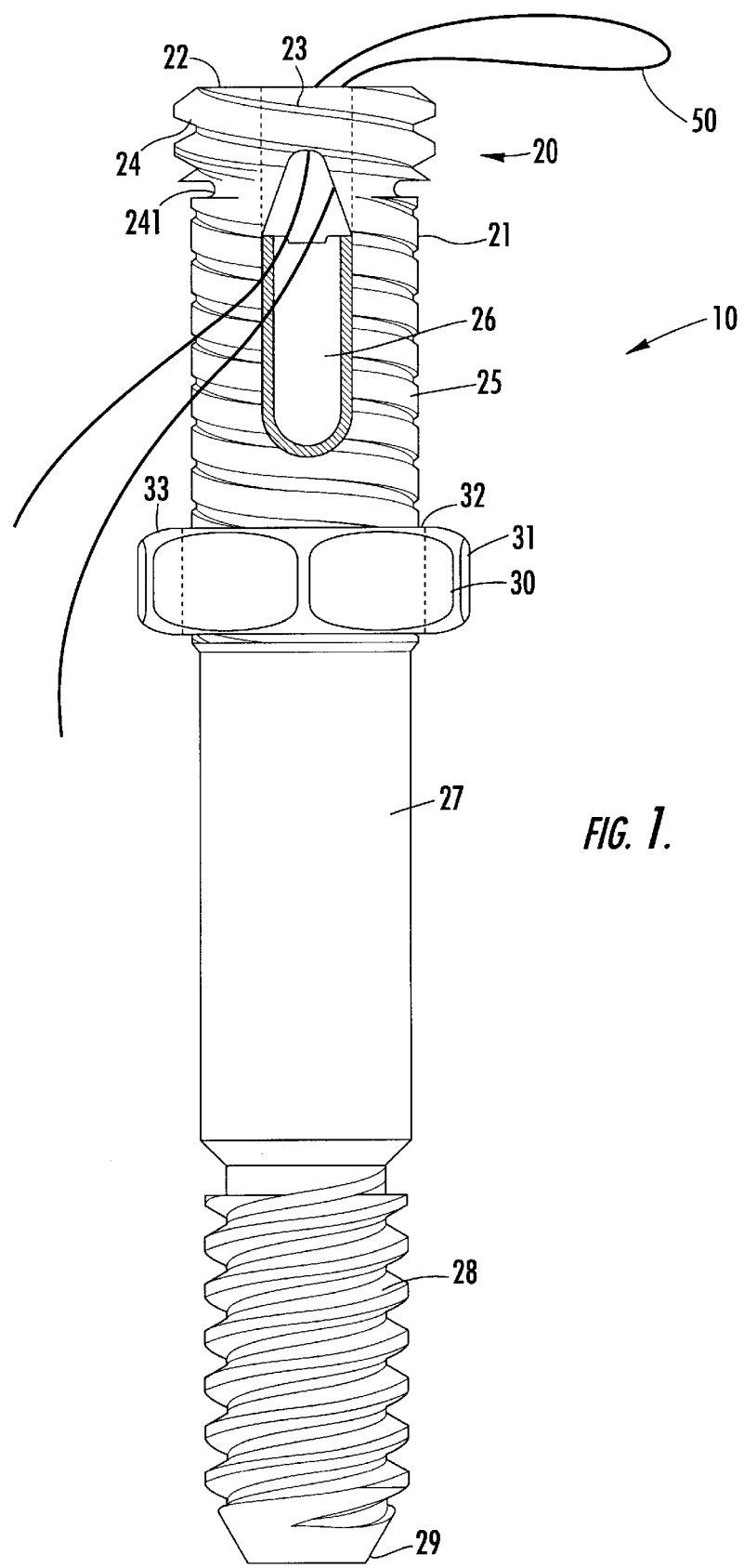
FIG. 1 is a perspective side view of a first embodiment of the connector of the present invention in the open position.
Figure 2:
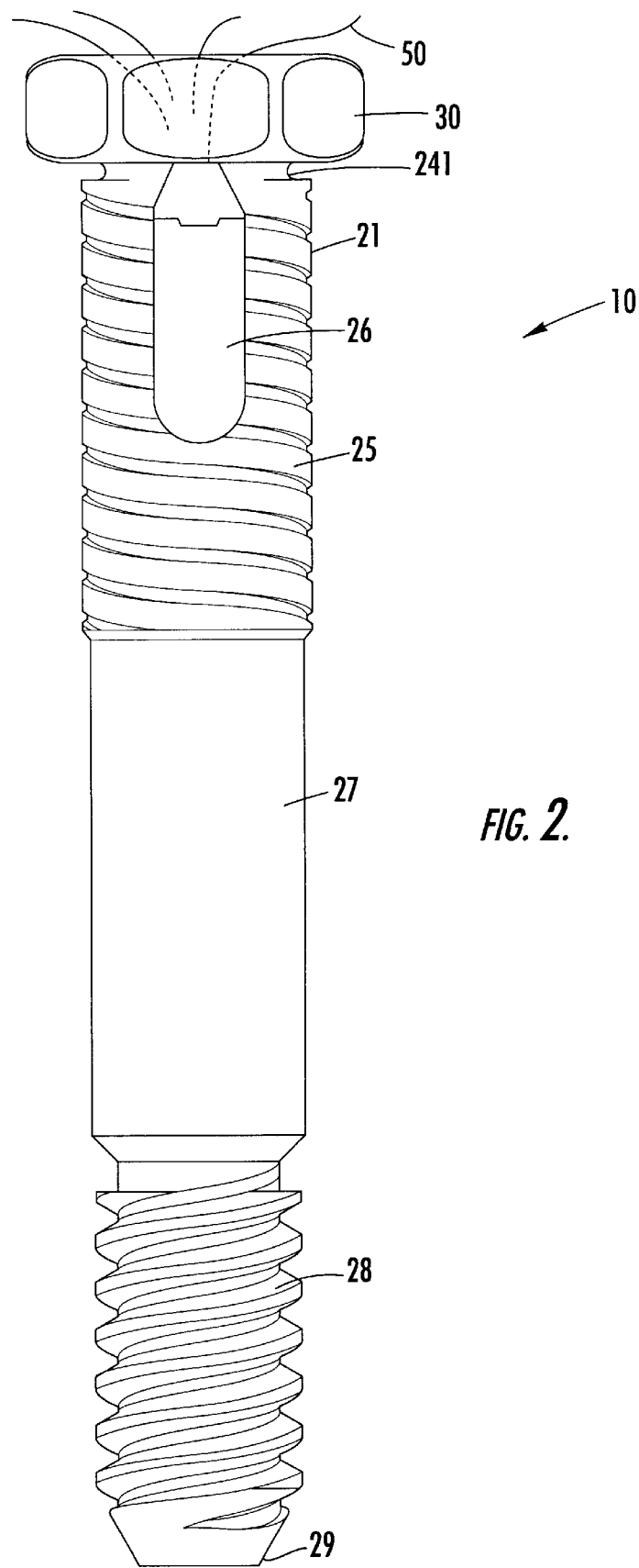
FIG. 2 is a perspective side view of the connector of FIG. 1 in the locked position.
Figure 3:
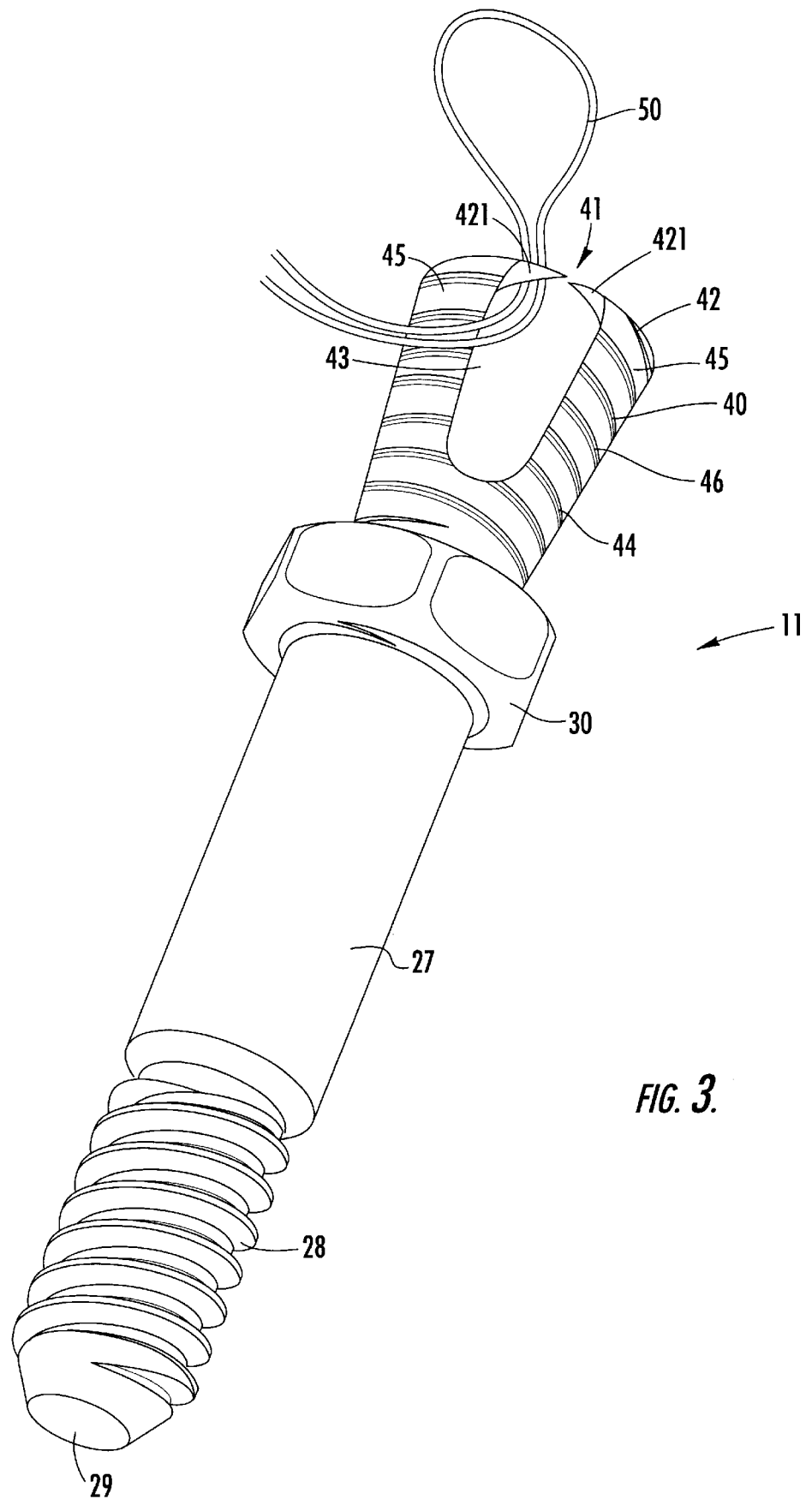
FIG. 3 is a perspective side view of an alternate embodiment of a connector.

A first embodiment of the connector is illustrated in FIGS. 1 and 2. This embodiment of a connector 10 is for affixing at least one piece of flexible, elongated material, here shown as a loop of suture 50, at a surgical site. The connector 10 comprises a locking member 20 that has an engagement portion, here a threaded outer surface 21 along a section adjacent the proximal end 22. The locking member 20 also has means for supporting the suture 50 at the proximal end 22.

In this embodiment the support means comprises a longitudinal bore 23 that extends from the proximal end 22 and an enlarged head 24 at the proximal end 22. A shaft portion 25 extends distally from the head 24. The shaft 25 has at least one side portal, here, two side portals 26, adjacent and distal of the head 24 and communicating with the bore 23. In use the flexible material 50 is passed into the bore 23 from the proximal end 22 and out through one of the side portals 26.

In this embodiment the shaft portion 25 has a threaded outer surface, as does the head 24. Preferably the threading has a first handedness.

Formed integrally with the locking member 20 in this embodiment is an extension of the shaft 25, proceeding distally and generally collinearly therefrom. A central portion 27 extending distal of the shaft 25 is generally cylindrical and nonthreaded. A distal portion 28 extending distal of the central portion 27 is threaded up to the distal end 29, preferably with a second handedness opposite the first. The distal portion 28 is for affixing to a deployment instrument. The distal end 29 is preferably narrowed to facilitate engagement with the deployment instrument.

In a preferred embodiment the locking member 20 has a frangible region 241, here shown as being just distal of the head 24.

The connector 10 further comprises an outer member that has means for receiving the locking member's threaded engagement portion 21. In this embodiment the outer member comprises a nut 30 whose outer surface 31 comprises a generally hexagonal shape for mating with a deployment instrument bore having a commensurately hexagonal shape. This shape is not intended to be limiting, however, and one of skill in the art will recognize that other shapes will provide similar drivability.

The nut 30 has a bore 32 extending from the proximal end 33, the bore 32 being dimensioned to admit the shaft 25 but to prevent passage past the head 24. Here the nut's bore 32 is threaded for engaging the shaft 25. The nut 30 is movable by means of a screwing motion, the nut 30 moving in a proximal direction, between a disengaged position and a locking position in cooperation with the locking member's head 24 and portal(s) 26. Specifically, in the disengaged position, at least a portion of the portal 26 is uncovered, and, in the locking position, at least a portion of the portal 26 is sufficiently occluded to prevent a movement of flexible material 50 passing therethrough with respect to the connector 10.

When the nut 30 is in the locking position, the suture 50 achieves a nonlinear path relative to the shaft's threaded portion 21 and the nut's bore 32. This nonlinear, serpentine path comprises an insertion into the locking member's bore 23, a proceeding out the portal 26 generally proximally between the locking member's outer surface 21 and the inner surface of the nut's bore 32, and an exit between the locking member's head 24 and shaft 25 and the nut's proximal end 33. Such a pathway serves to restrain the suture 50 against movement between the locking member 20 and the nut 30. Specifically, a pressing of the suture 50 between the nut's bore 32 and the shaft's threaded portion 25 and head 24 possesses sufficient friction to lock the suture 50 in a desired position.

Another feature of the connector 10 is that the mode of engagement between the locking member 20 and the nut 30 permits a placement and a locking therebetween at a desired surgical site in a generally collinear fashion with the suture material ends 50, one of the desired objectives.

A second embodiment of the connector 11 (FIG. 3) comprises a locking member 40 that has a longitudinal bore 41 extending from the proximal end 42. At least one slot, here two slots 43, extend from the proximal end 42 through a side wall 44 and are in communication with the bore 41. Two generally opposed top portions 421 of the locking member 40 meet across the slots 43 and are relatively slidable across each other.

A top portion of the locking member 40 encompassing the slots 43 is movable between a first position having a first diameter and a second position having a second diameter larger than the first diameter. Here the slots 43 form the top portion into "petals" 45 that are biased outward, that is, to the second position.

As above, the locking member 40 has a threaded outer surface along a shaft section 46 adjacent the proximal end 42. Preferably the threading has a first handedness.

In this embodiment the support means comprises the longitudinal bore 41 and the slots 43. In use the flexible material 50 is passed into the bore 41 from the proximal end 42 and out through one of the slots 43.

In this embodiment the shaft extension and the nut 30 are substantially the same as in the first embodiment. Here the nut 30 is moved proximally, squeezing the slots 43 into the first position, and thereby, because of the biasing, retaining the nut 30 thereupon, with a piece of suture 50, for example, being retained therebetween.

Figure 4:
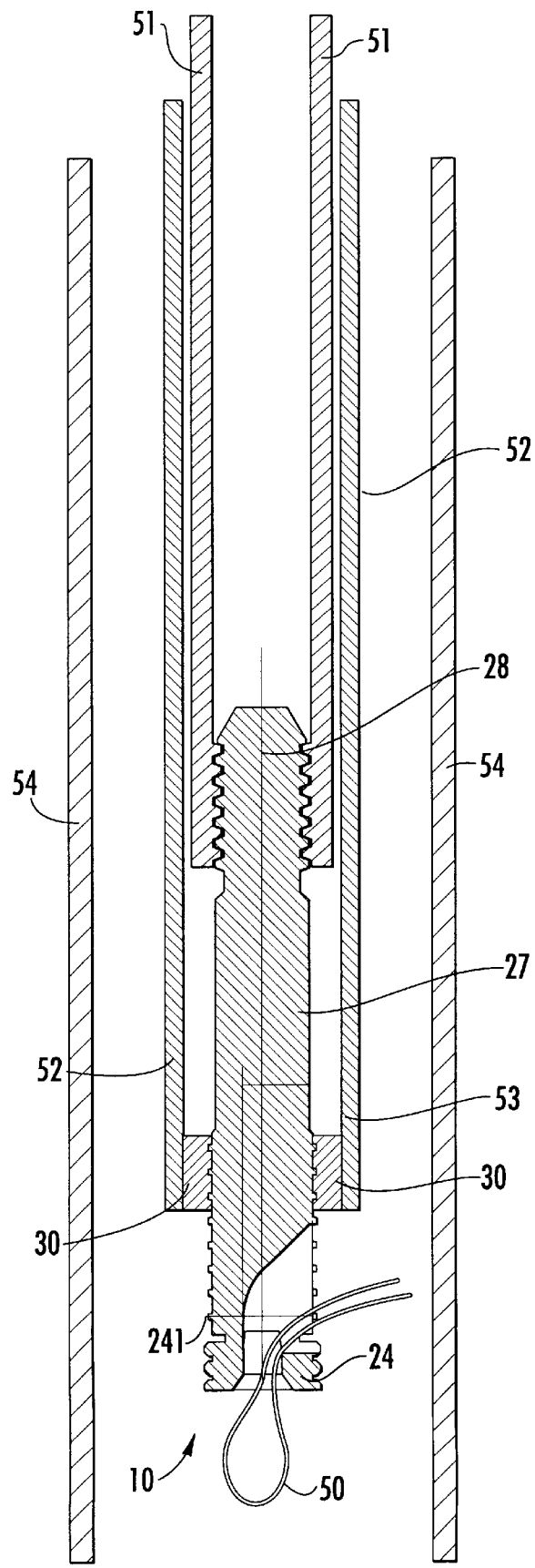
FIG. 4 is a side cross-sectional view of a delivery system for the connector.

The connectors 10,11 may be delivered by sliding the locking member 20,40 and nut 30 within a trocar cannula 54, thereby permitting use in endoscopic surgery (FIG. 4). A extension piece 51 is screwable onto the distal threaded portion 28. Further, a nut driver 52, which comprises a generally cylindrical member, passes over the extension piece 51 and the central 27 and distal 28 portions of the locking member 20 and engages the nut 30 by means of a bore 53 adapted to drive the nut 30. The nut 30 is advanced in a proximal direction by screwing the nut driver 52, until the nut reaches the head 24 and the suture 50 is trapped. The nut driver 52 is removed and the frangible attachment 241 is broken, leaving the connector 10 in place at the desired surgical site.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A connector for affixing at least one piece of flexible, elongated material at a surgical site, the connector comprising:
   a locking member having an engagement portion adjacent a proximal end and means for supporting a flexible member at the proximal end;
   an outer member having means for receiving the locking member engagement portion, the outer member movable between a disengaged position and a locking position in cooperation with the flexible member supporting means; and
   means for causing a piece of flexible material to achieve a nonlinear path relative to the locking member engagement portion and the outer member receiving means, wherein when the outer member is in the locking position the flexible material piece is retainable along the nonlinear path against movement between the locking member and the outer member, the causing means further adapted to permit a placement and a locking of the outer member and the locking member at a desired surgical site in a generally collinear fashion with the flexible material piece.

2. The connector recited in claim 1, wherein:
   the locking member has a longitudinal bore extending from the proximal end, an enlarged head at the proximal end, and a shaft extending distally from the head, the shaft having a side portal adjacent and distal of the head and communicating with the bore; and
   the outer member has a bore extending from a proximal end, the bore dimensioned to admit the shaft but to prevent admission of the head, the outer member movable along the shaft between the disengaged position, wherein at least a portion of the portal is uncovered, and the locking position proximal of the disengaged position, wherein at least a portion of the portal is occluded;
   wherein in the locking position a serpentine path is provided for the piece of material comprising an insertion through the locking member bore, a proceeding out the portal generally proximally between a locking member outer surface and an outer member bore inner surface, and an exit between the locking member head and shaft and the outer member proximal end.

3. The connector recited in claim 2, wherein at least a portion of the shaft has a threaded exterior surface and at least a portion of the outer member bore inner surface is threaded for engaging the shaft threaded portion, the locking position achievable by screwing the outer member along the shaft until the portal is at least partly occluded.

4. The connector recited in claim 3, wherein the locking member further has means for affixing to a deployment instrument adjacent a distal end.

5. The connector recited in claim 4, wherein:
   the threaded shaft portion comprises a first threaded portion; and
   the affixing means comprises a second threaded portion adjacent the distal end in spaced relation from the first threaded portion.

6. The connector recited in claim 5, wherein the outer member has means on an outer surface for being driven by a deployment instrument.

7. The connector recited in claim 5, wherein the outer member has a noncircular outer surface adapted to fit within a bore of a deployment instrument having a shape adapted to drive the outer member.

8. The connector recited in claim 7, wherein the outer member comprises a nut and the nut outer surface comprises a generally hexagonal shape for mating with a deployment instrument bore having a generally hexagonal shape.

9. The connector recited in claim 8, wherein a pressing of the flexible material between a bore of the nut and the first threaded shaft portion possesses sufficient friction to lock the flexible material in a desired position.

10. The connector recited in claim 3, wherein a lower section of the shaft is removable adjacent a bottom end of the outer member.

11. The connector recited in claim 10, wherein the flexible material comprises two ends of a loop of suture material.

12. The connector recited in claim 1, wherein the locking member and the outer member are slidable within a trocar cannula, thereby permitting use in endoscopic surgery.

13. The connector recited in claim 1, further comprising an insertion shaft, the locking member frangibly attached at a distal end to a proximal end of the insertion shaft for permitting a breaking of the frangible attachment following a movement from the disengaged position to the locking position.

14. A connector for affixing at least one piece of flexible, elongated material at a surgical site, the connector comprising:
   a locking member having:
      a longitudinal bore extending from a proximal end;
      at least one slot extending from the proximal end through a side wall and in communication with the bore, a top portion of the locking member encompassing the slot movable between a first position having a first diameter and a second position having a second diameter larger than the first diameter and biased to the second position;
      an engagement portion at a distal end; and
      means for supporting a flexible member at a proximal end;
   an outer member having means for receiving the locking member engagement portion, the outer member movable between an disengaged position and a locking position in cooperation with the flexible member supporting means; and
   means for causing a piece of flexible material to achieve a nonlinear path relative to the locking member engagement portion and the outer member receiving means, wherein when the outer member is in the locking position the flexible material piece is retainable along the nonlinear path against movement between the locking member and the outer member, the causing means further adapted to permit a placement and a locking of the outer member and the locking member at a desired surgical site in a generally collinear fashion with the flexible material piece.

15. The device recited in claim 14, wherein the slot comprises a pair of generally diametrically opposed slots.

16. The device recited in claim 14, wherein the locking member outer surface is at least partially threaded from the proximal end, and wherein outer member comprises a nut having a threaded bore dimensioned to pass onto the locking member in the first position and to be retained by the locking member in the second position.

17. A method for affixing a piece of flexible material at a surgical site, the method comprising the steps of:
- passing a piece of flexible material through a passage in a generally cylindrical locking member;
- passing a generally cylindrical outer member over the locking member in covering relation to at least a portion of the passage, at least a portion of the locking member dimensioned to closely engage a bore of the outer member, the flexible material proceeding between the locking member outer surface and the outer member bore inner surface to form a serpentine pathway; and
- retaining at least a portion of the inner member within the outer member bore to form a locked position therebetween.

* * * * *